(12) United States Patent
Teoh et al.

(10) Patent No.: US 10,279,108 B2
(45) Date of Patent: May 7, 2019

(54) SAFETY NEEDLE ASSEMBLIES AND RELATED METHODS

(71) Applicant: B. Braun Melsungen AG, Melsungen (DE)

(72) Inventors: Teng Sun Teoh, Penang (MY); Mohd Zairizal bin Zakaria, Penang (MY); Hwa Loon Chan, Penang (MY)

(73) Assignee: B. Braun Melsungen AG, Melsungen (DE)

(*) Notice: Subject to any disclaimer, the term of this patent is extended or adjusted under 35 U.S.C. 154(b) by 115 days.

(21) Appl. No.: 15/115,884

(22) PCT Filed: Feb. 6, 2015

(86) PCT No.: PCT/EP2015/052521
§ 371 (c)(1),
(2) Date: Aug. 1, 2016

(87) PCT Pub. No.: WO2015/118109
PCT Pub. Date: Aug. 13, 2015

(65) Prior Publication Data
US 2017/0165417 A1 Jun. 15, 2017

Related U.S. Application Data

(60) Provisional application No. 61/937,307, filed on Feb. 7, 2014.

(51) Int. Cl.
*A61M 5/158* (2006.01)
*A61M 5/32* (2006.01)

(52) U.S. Cl.
CPC ............ *A61M 5/158* (2013.01); *A61M 5/326* (2013.01); *A61M 5/3271* (2013.01);
(Continued)

(58) Field of Classification Search
CPC ...... A61M 2005/1586; A61M 2207/00; A61M 5/158
See application file for complete search history.

(56) References Cited

U.S. PATENT DOCUMENTS

| | | |
|---|---|---|
| 5,049,136 A | 9/1991 | Johnson |
| 2009/0259196 A1 | 10/2009 | Gratwohl et al. |

FOREIGN PATENT DOCUMENTS

| | | |
|---|---|---|
| EP | 1321158 A1 | 6/2003 |
| RU | 2438721 C2 | 1/2012 |

OTHER PUBLICATIONS

International Search Report and Written Opinion on corresponding PCT application (PCT/EP2015/052521) from International Searching Authority (EP) dated May 6, 2015.
(Continued)

*Primary Examiner* — Imani N Hayman
(74) *Attorney, Agent, or Firm* — Klein, O'Neill & Singh, LLP

(57) ABSTRACT

The safety needle assembly comprises a housing including a proximal end and a distal end and defining an interior space. A barrel is rotatably received within the interior space of the housing. A needle hub is received within the proximal end of the housing. A needle, including a sharp distal tip, extends distally from the needle hub, through the barrel, and through the distal end of the housing. A safety shield defining a lumen is received within the interior space of the housing. The safety shield extends distally from the housing through the distal end of the housing. The needle extends through the lumen of the safety shield with the sharp distal tip exposed from the safety shield. A biasing member is received within the barrel and extends between the needle hub and the safety shield. The safety needle assembly includes a first configuration in which the safety shield and the barrel define a first relative rotational orientation, and a
(Continued)

second configuration in which the safety shield and the barrel define a second relative rotational orientation.

21 Claims, 10 Drawing Sheets

(52) U.S. Cl.
CPC ............ *A61M 2005/1586* (2013.01); *A61M 2005/3247* (2013.01); *A61M 2005/3267* (2013.01); *A61M 2207/00* (2013.01)

(56) References Cited

OTHER PUBLICATIONS

Office Action on corresponding foreign application (RU Application No. 2016135932) from the Russian Intellectual Property Office dated Mar. 30, 2018.

Office Action on corresponding foreign application (EP Application No. 15702807.7) from the European Patent Office dated Jun. 14, 2018.

Decision to Grant on corresponding foreign application (RU Application No. 2016135932) from the Russian Patent Office dated Sep. 26, 2018.

SAFETY NEEDLE ASSEMBLIES AND RELATED METHODS

CROSS-REFERENCE TO RELATED APPLICATION

This application claims priority and benefit of U.S. provisional application No. 61/937,307, filed Feb. 7, 2014, the contents of which are expressly incorporated herein by reference.

TECHNICAL FIELD

The present embodiments relate to assemblies and methods for percutaneously infusing fluids to a body and/or withdrawing fluids from a body.

BACKGROUND

Needle assemblies are commonly used to percutaneously infuse fluids to a body and/or withdraw fluids from a body. The needle assembly generally remains disposed in the vasculature while one or more assemblies are connected and disconnected to the assembly to complete the infusion/withdrawal process. Upon withdrawing the assembly from the vasculature, the sharp distal tip of the needle is exposed. It is disadvantageous to leave the tip exposed, as there is a risk that medical staff can accidentally prick themselves. This phenomenon is known as needlestick, and can transfer blood-borne diseases.

SUMMARY

The various embodiments of the present safety needle assembly and methods have several features, no single one of which is solely responsible for their desirable attributes. Without limiting the scope of the present embodiments as expressed by the claims that follow, their more prominent features now will be discussed briefly. After considering this discussion, and particularly after reading the section entitled "Detailed Description," one will understand how the features of the present embodiments provide the advantages described herein.

One of the present embodiments comprises a safety needle assembly. The safety needle assembly comprises a housing including a proximal end and a distal end and defining an interior space. The safety needle assembly further comprises a barrel rotatably received within the interior space of the housing. The safety needle assembly further comprises a needle hub received within the proximal end of the housing. The safety needle assembly further comprises a needle extending distally from the needle hub, through the barrel, and through the distal end of the housing. The needle includes a sharp distal tip. The safety needle assembly further comprises a safety shield defining a lumen and received within the interior space of the housing. The safety shield extends distally from the housing through the distal end of the housing. The needle extends through the lumen of the safety shield with the sharp distal tip exposed from the safety shield. The safety needle assembly further comprises a biasing member received within the barrel and extending between the needle hub and the safety shield. The safety needle assembly includes a first configuration in which the safety shield and the barrel define a first relative rotational orientation, and a second configuration in which the safety shield and the barrel define a second relative rotational orientation.

Another of the present embodiments comprises a method of using a safety needle assembly including a housing supporting a barrel and a needle hub, the barrel being rotatably received within the housing, a needle extending distally from the needle hub and including a sharp distal tip, a safety shield being disposed over the needle. The method comprises, with the safety needle assembly in a first configuration in which the sharp distal tip of the needle is exposed from a distal end of the safety shield and the safety shield engages the barrel to prevent translation of the safety shield distally along the needle, translating the safety shield proximally along the needle. The method further comprises rotating the barrel with respect to the safety shield as the safety shield translates proximally along the needle, thereby disengaging the safety shield from the barrel to permit translation of the safety shield distally along the needle. The method further comprises translating the safety shield distally along the needle until the safety shield covers the sharp distal tip of the needle.

A still further aspect of the present disclosure is a safety needle assembly comprising: a housing including a proximal end and a distal end, the housing defining an interior space; a barrel rotatably received within the interior space of the housing; a needle hub received within the proximal end of the housing; a needle extending distally from the needle hub, through the barrel, and through the distal end of the housing, the needle including a sharp distal tip; a safety shield defining a lumen and received within the interior space of the housing, the safety shield extending distally from the housing through the distal end of the housing, the needle extending through the lumen of the safety shield with the sharp distal tip exposed from the safety shield; and a biasing member received within the barrel and extending between the needle hub and the safety shield; wherein the safety needle assembly includes a first configuration in which the safety shield and the barrel define a first relative rotational orientation; and wherein the safety needle assembly includes a second configuration in which the safety shield and the barrel define a second relative rotational orientation.

The safety needle assembly wherein when the safety needle assembly occupies the first configuration the safety shield can engage the barrel to prevent distal translation of the safety shield relative to the needle.

The safety needle assembly wherein the safety shield can include a detent that engages a notch on the barrel when the safety needle assembly occupies the first configuration.

The safety needle assembly wherein the notch can include a sloped surface proximal of the detent.

The safety needle assembly wherein the detent can bear against the sloped surface when the safety shield moves proximally relative to the barrel, causing the barrel to rotate relative to the safety shield toward the second relative rotational orientation.

The safety needle assembly wherein the detent can extend radially outward from the safety shield.

The safety needle assembly wherein the barrel can include a longitudinal channel and the detent can slide within the channel when the safety shield and the barrel occupy the second relative rotational orientation.

The safety needle assembly wherein when the safety needle assembly occupies the second configuration the barrel does not have to constrain distal translation of the safety shield relative to the needle.

The safety needle assembly wherein the biasing member can bias the safety shield in the distal direction when the safety needle assembly occupies the first configuration and when the safety needle assembly occupies the second configuration.

The safety needle assembly wherein the safety shield can move distally relative to the needle to cover the sharp distal tip of the needle when a distally directed force exerted by the biasing member on the safety shield overcomes a proximally directed force exerted on the safety shield.

The safety needle assembly wherein when the safety shield covers the sharp distal tip of the needle the housing can prevent the safety shield from moving proximally with respect to the needle by a distance sufficient to expose the sharp distal tip of the needle.

The safety needle assembly wherein the housing can include a catch configured to deflect to allow the safety shield to pass when the safety shield moves in the proximal-to-distal direction relative to the housing and can be configured to block movement of the safety shield in the distal-to-proximal direction relative to the housing.

The safety needle assembly wherein the catch can comprise a leaf spring.

The safety needle assembly wherein the safety shield can engage the housing to prevent the safety shield from rotating relative to the housing.

The safety needle assembly wherein the safety shield can include at least one rail that extends longitudinally along an outer surface of the safety shield and that can slidably receive within at least one indentation in the housing.

The safety needle assembly can further comprise a wing assembly including wings extending laterally from the safety needle assembly and configured to facilitate securing the safety needle assembly to a patient.

The safety needle assembly wherein the biasing member can be a spring.

Another aspect of the present disclosure includes a method of manufacturing a safety needle assembly. The method can comprise: forming a housing supporting a barrel and a needle hub, the barrel being rotatably received within the housing; extending a needle distally from the needle hub, said needle including a sharp distal tip; positioning a safety shield over the needle so that the sharp distal tip is exposed from a distal end of the safety shield in a first configuration; wherein the safety shield engages the barrel to prevent translation of the safety shield distally along the needle; wherein the barrel is rotatable with respect to the safety shield when the safety shield translates proximally along the needle to disengage the safety shield from the barrel to permit translation of the safety shield distally along the needle; and wherein the safety shield is translatable distally along the needle to cover the sharp distal tip of the needle.

The method can further comprise a biasing member to apply a distally directed force to the safety shield.

The method wherein the biasing member can be received within the barrel and extends between the needle hub and the safety shield.

The method wherein the biasing member can be a spring.

The method wherein the safety shield can include a detent that engages a catch on the barrel when the safety needle assembly occupies the first configuration.

The method wherein the catch can include a sloped surface proximal of the detent.

The method wherein the detent can bear against the sloped surface when the safety shield translates proximally along the needle, causing the barrel to rotate with respect to the safety shield.

Another aspect of the present disclosure is a method of using a safety needle assembly. The method of using can include a housing supporting a barrel and a needle hub, the barrel being rotatably received within the housing, a needle extending distally from the needle hub and including a sharp distal tip, a safety shield being disposed over the needle, the method comprising: with the safety needle assembly in a first configuration in which the sharp distal tip of the needle is exposed from a distal end of the safety shield and the safety shield engages the barrel to prevent translation of the safety shield distally along the needle, translating the safety shield proximally along the needle; rotating the barrel with respect to the safety shield as the safety shield translates proximally along the needle, thereby disengaging the safety shield from the barrel to permit translation of the safety shield distally along the needle; and translating the safety shield distally along the needle until the safety shield covers the sharp distal tip of the needle.

The method of using wherein translating the safety shield distally along the needle can comprise a biasing member applying a distally directed force to the safety shield.

The method of using wherein the biasing member can be received within the barrel and extends between the needle hub and the safety shield.

The method of using wherein the biasing member can be a spring.

The method of using wherein the safety shield can include a detent that engages a catch on the barrel when the safety needle assembly occupies the first configuration.

The method of using wherein the catch can include a sloped surface proximal of the detent.

The method of using wherein the detent can bear against the sloped surface when the safety shield translates proximally along the needle, causing the barrel to rotate with respect to the safety shield.

The method of using wherein when the safety shield covers the sharp distal tip of the needle, the housing can prevent the safety shield from moving proximally with respect to the needle by a distance sufficient to expose the sharp distal tip of the needle.

The method of using wherein the housing can include a catch configured to deflect to allow the safety shield to pass when the safety shield moves in the proximal-to-distal direction relative to the housing and configured to block movement of the safety shield in the distal-to-proximal direction relative to the housing.

The method wherein the catch can comprise a leaf spring.

BRIEF DESCRIPTION OF THE DRAWINGS

The various embodiments of the present safety needle assembly and methods now will be discussed in detail with an emphasis on highlighting the advantageous features. These embodiments depict the novel and non-obvious safety needle assembly and methods shown in the accompanying drawings, which are for illustrative purposes only. These drawings include the following figures, in which like numerals indicate like parts.

DETAILED DESCRIPTION

Figure 1:
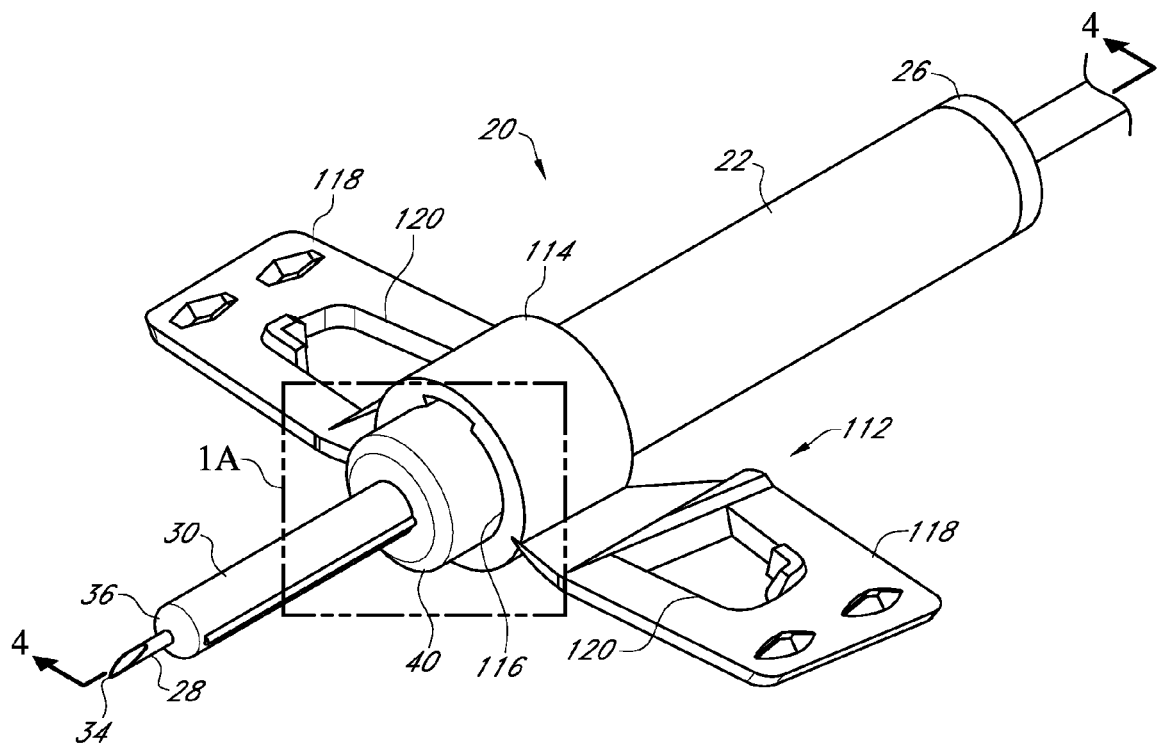
FIG. 1 is a side perspective view of one embodiment of the present safety needle assembly, illustrating the assembly in a pre-activation configuration.

The following detailed description describes the present embodiments with reference to the drawings. In the drawings, reference numbers label elements of the present embodiments. These reference numbers are reproduced below in connection with the discussion of the corresponding drawing features.

The embodiments of the present safety needle assemblies and related methods are described below with reference to the figures. These figures, and their written descriptions, indicate that certain components of the apparatus are formed integrally, and certain other components are formed as separate pieces. Those of ordinary skill in the art will appreciate that components shown and described herein as being formed integrally may in alternative embodiments be formed as separate pieces. Those of ordinary skill in the art will further appreciate that components shown and described herein as being formed as separate pieces may in alternative embodiments be formed integrally. Further, as used herein the term integral describes a single unitary piece.

The present embodiments include methods of using a safety needle assembly and method of manufacturing or making the safety needle assembly. Some of these embodiments may be performed in connection with treating a human and/or animal body. Others of these embodiments may be performed independently of a human and/or animal body, such as for purposes of testing or demonstration. Accordingly, the present embodiments pertaining to methods of using a safety needle assembly should not be construed as limited to methods of treating a human and/or animal body.

Figure 2:
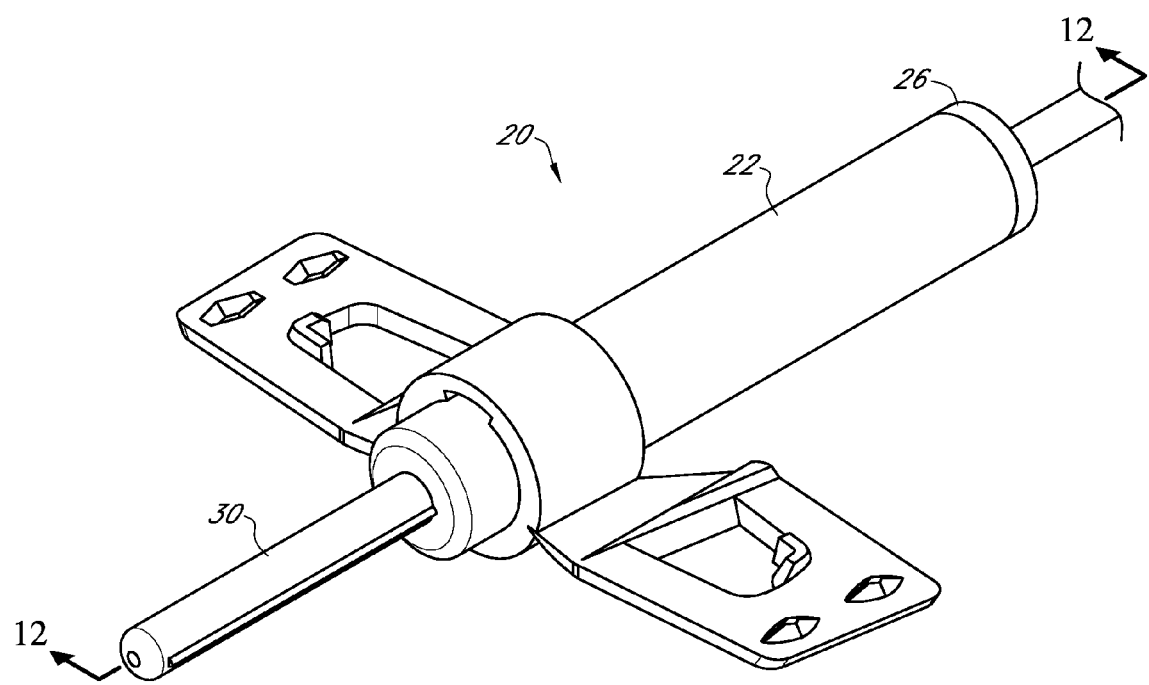
FIG. 2 is a side perspective view of the safety needle assembly of FIG. 1, illustrating the assembly in a post-activation configuration.
Figure 3:
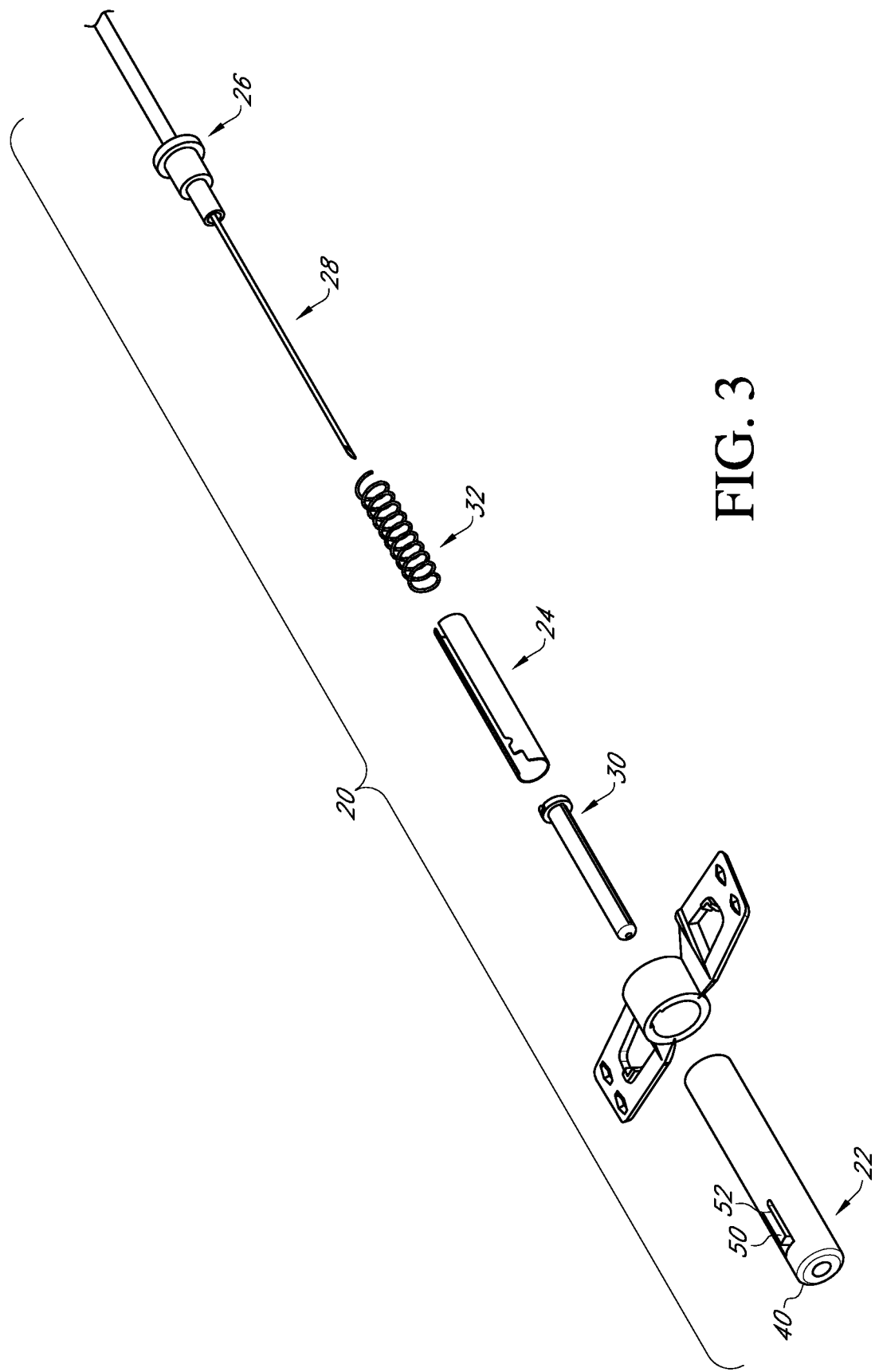
FIG. 3 is an exploded side perspective view of the safety needle assembly of FIG. 1.

FIGS. 1-12 illustrate one embodiment of the present safety needle assembly 20. The assembly 20 is configured for use in drawing blood and/or infusing blood or other liquids. With reference to FIGS. 1, 2, and 3, in some embodiments the assembly 20 includes a housing 22, a barrel 24 (FIG. 3), a needle hub 26, a needle 28, a safety shield 30, and a biasing member 32 (FIG. 3). With reference to FIG. 1, the needle 28 includes a sharp distal tip 34. In the pre-activation or ready to use configuration of FIG. 1, the sharp distal tip 34 is exposed from a distal end 36 of the safety shield 30. The assembly 20 may optionally include a removable cap (not shown) that extends over the needle 28 and the safety shield 30 in the pre-activation configuration to cover the sharp distal tip 34 and thereby reduce the likelihood of needlestick and/or for packaging. In the post-activation configuration of FIG. 2, also referred to as the protective or protected position, the safety shield 30 extends distally beyond the sharp distal tip 34 to protectively cover the sharp tip 34 and reduce the likelihood of unintended needlestick.

Figure 4:
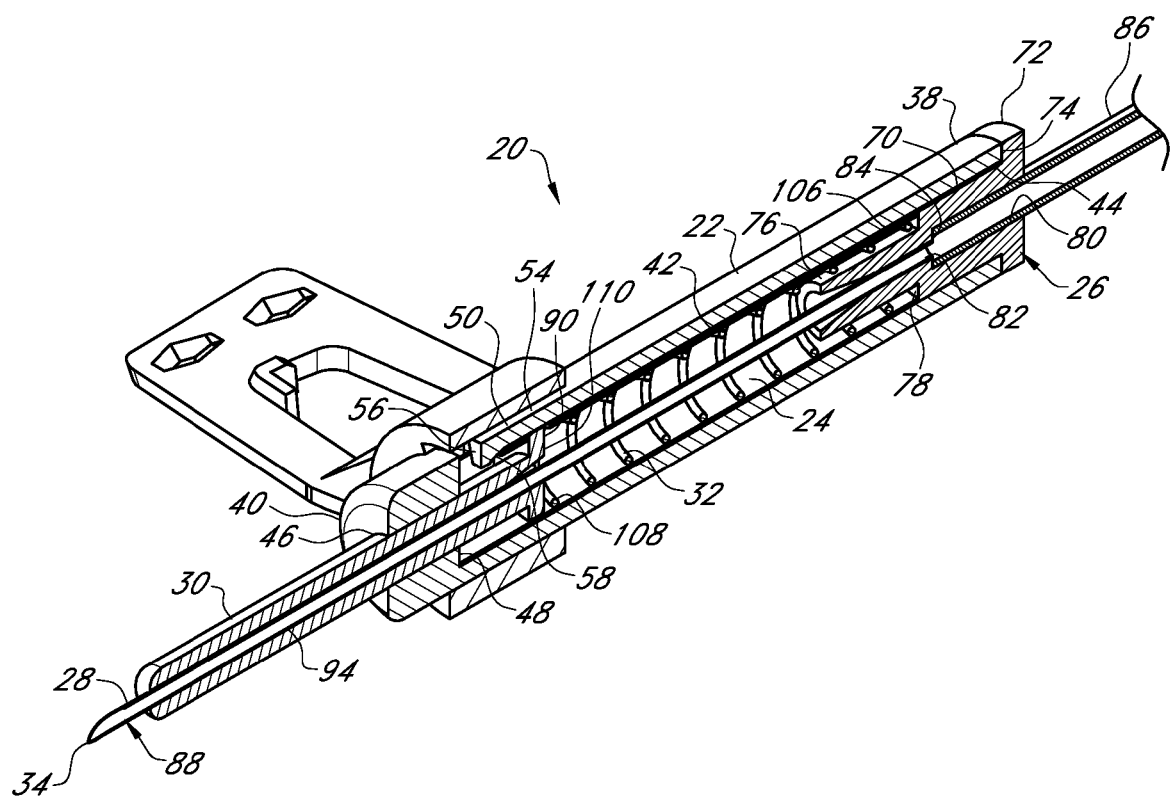
FIG. 4 is a cross-sectional side perspective view of the safety needle assembly of FIG. 1 taken through the cut line labeled 4-4 in FIG. 1.

With reference to FIG. 4, the housing 22 includes a proximal end 38 and a distal end 40, and defines an interior space 42. In the illustrated embodiment, the housing 22 is generally cylindrical. However, the illustrated configuration is just one example and is not limiting. The housing 22 includes a proximal opening 44 at the proximal end 38 and a distal opening 46 at the distal end 40. A wall thickness of the housing 22 is substantially uniform, except at the distal end 40, where the housing wall is thicker, creating a proximally facing internal annular shoulder 48 at the point where the wall thickness increases. In alternative embodiments, the wall thickness of the housing 22 need not be thicker at the distal end 40. For example, ribs (not shown) or other structure could be provided at or near the distal end 40 to serve the same, or a similar, function as the shoulder 48. The distal opening 46, which extends through the region of increased wall thickness, thus has a smaller diameter than the proximal opening 44. In other examples, the housing has a uniform thickness and the shoulder is formed from a separately inserted or co-molded component.

With reference to FIGS. 3 and 4, the housing 22 includes a catch 50 near the distal end 40. With particular reference to FIG. 3, the catch 50 comprises a portion of the wall surface of the housing 22 defined by a U-shaped cutout 52 through the sidewall. With particular reference to FIG. 4, the catch 50 is a cantilevered leaf spring that extends distally from its junction 54 with the sidewall. The junction 54 can be proximally located as shown or distally located. Near its distal end 56, a thickness of the catch 50 increases, creating a ramped surface 58. As described below, the ramped surface 58 bears against the safety shield 30 as the safety shield 30 slides distally along the needle 28, causing the catch 50 to deflect radially outward until the safety shield 30 passes the catch 50. After the safety shield 30 passes the catch 50, a spring return force in the deflected catch 50 causes the catch 50 to return to its at rest position in which it blocks the safety shield 30 from returning proximally along the needle 28. The process by which the safety shield 30 deflects the catch 50 and the catch subsequently blocks the safety shield's return is described in detail below.

Figure 5:
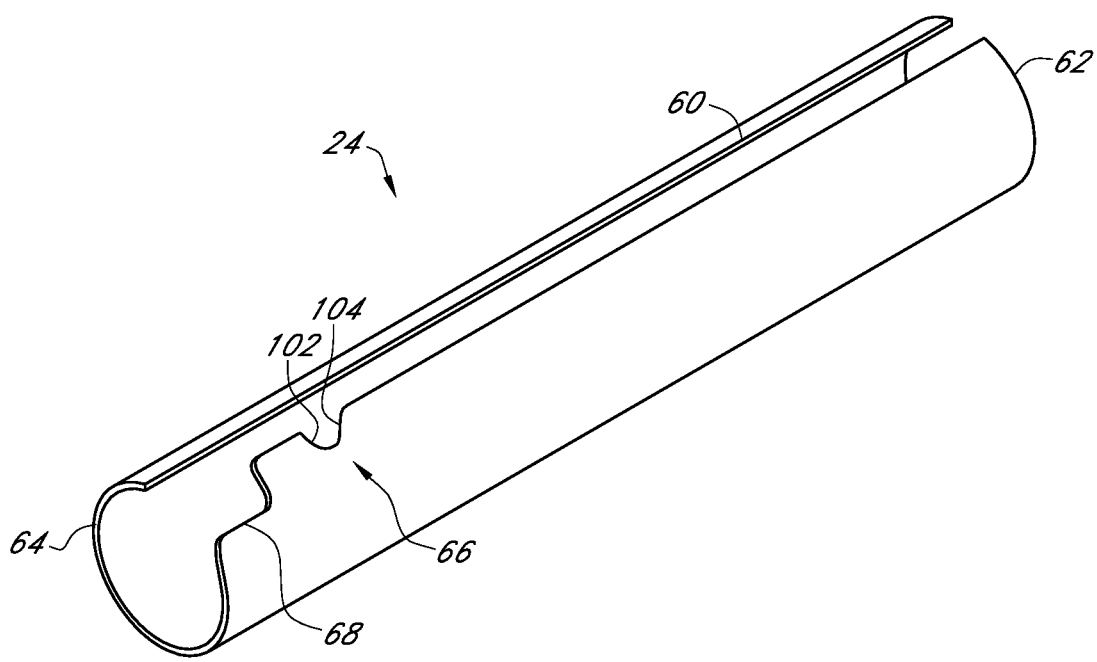
FIG. 5 is a side perspective view of the barrel of the safety needle assembly of FIG. 1.

With further reference to FIG. 4, the barrel 24 is rotatably received within the interior space 42 of the housing 22. Relative dimensions of the barrel 24 and the housing 22 are preferably such that the barrel 24 is freely rotatable within the interior space 42 of the housing 22 without substantial friction between the barrel 24 and the housing 22. FIG. 5 illustrates the barrel 24 in greater detail. In the illustrated embodiment, the barrel 24 is generally cylindrical and includes a substantially uniform wall thickness. However, the illustrated configuration is just one example and is not limiting. A channel 60 extends through the sidewall of the barrel 24 from its proximal end 62 to its distal end 64. An edge of the channel 60 includes a notch 66 adjacent the distal end 64. The notch 66 engages the safety shield 30, as described in detail below. Distal of the notch 66, the edge of the channel 60 further includes a cutout 68 at the distal end 64. The cutout 68 provides a clearance so that the barrel 24 does not interfere with the catch 50 on the housing 22. The notch 66 and the cutout 68 are not limited to their respective shapes as illustrated. In alternative embodiments either or both of the notch 66 and the cutout 68 may have different shapes.

With reference to FIG. 4, the needle hub 26 is received within the proximal opening 44 of the housing 22. In the illustrated embodiment, the needle hub 26 is shaped as a stepped cylinder. However, the illustrated configuration is just one example and is not limiting. A central portion 70 of the needle hub 26 includes an outer diameter that is slightly smaller than an inner diameter of the proximal opening 44 of the housing 22 such that the central portion 70 is snugly received and held within the proximal opening 44. The needle hub 26 may be held within the proximal opening 44 by any suitable means, such as a friction fit, adhesive, welding, etc. A proximal flange 72 extends radially outward of the central portion 70 at the proximal end of the needle hub 26 and abuts an annular proximal face 74 of the housing 22. A distal portion 76 of the needle hub 26 includes a lesser outer diameter than the central portion 70, creating a distally facing internal annular shoulder 78 at the junction of the distal portion 76 and the central portion 70.

With further reference to FIG. 4, the needle hub 26 further includes a first inner diameter 80 in the region of the central portion 70 that steps down to a second, lesser, inner diameter 82 near the junction of the central portion 70 and the distal portion 76, creating a proximally facing internal annular shoulder 84 at the location of the step. A tube 86 is received within the first inner diameter region 80 of the needle hub 26 and extends proximally out of the needle hub 26. The needle 28 is received within the lesser inner diameter 82 of the distal portion 76 of the needle hub 26 and extends distally from the needle hub 26, through the barrel 24, and through the distal opening 46 of the housing 22. The needle 28 may be held within the needle hub 26 by any suitable means, such as a friction fit, adhesive, welding, etc. As described above, the needle 28 includes a sharp distal tip 34. The needle 28, which may also be referred to as a cannula, further defines a lumen 88 that extends entirely through the needle 28. The lumen 88 of the needle 28 is in fluid communication with the tube 86 that extends proximally out of the needle hub 26. The tube 86 and the needle 28 thus create a fluid path between a fluid source connected to the tube 86 and a vessel of a patient in which the sharp distal tip 34 of the needle 28 is inserted.

Figure 6:
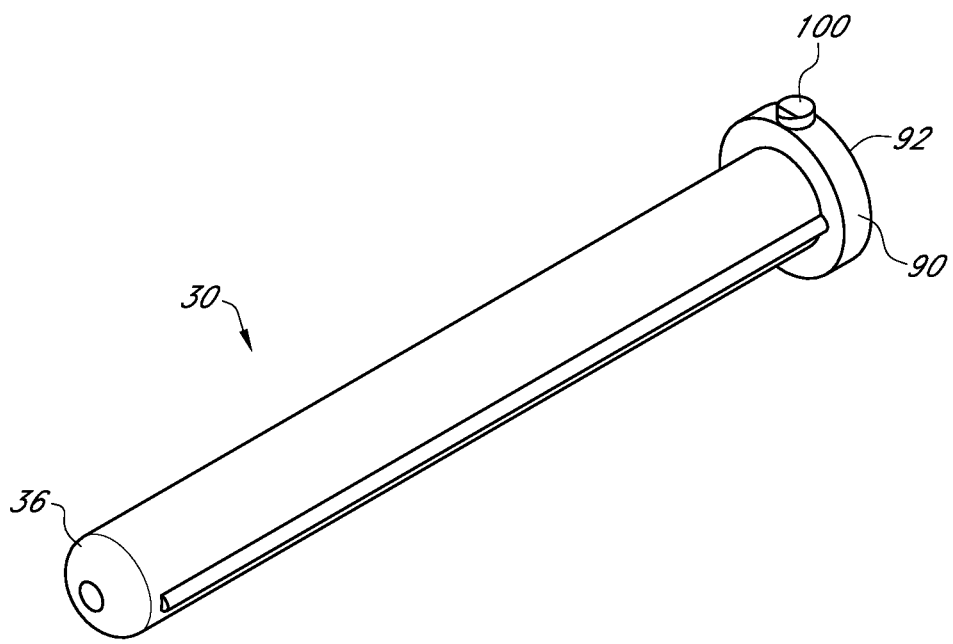
FIG. 6 is a side perspective view of the safety shield of the safety needle assembly of FIG. 1.

With further reference to FIG. 4, the safety shield 30 is received within the interior space 42 of the housing 22 and extends distally from the housing 22 through the distal opening 46. With reference to FIG. 6, which shows the safety shield 30 in detail, the safety shield 30 is shaped substantially as a cylinder having a uniform outer diameter, except for a tapered nose portion at the distal end 36 and a flange 90 that extends radially outward at the proximal end 92. With reference to FIG. 4, relative dimensions of the safety shield 30 and the distal opening 46 of the housing 22 are preferably such that the uniform outer diameter portion of the safety shield 30 is freely slidable within the distal opening 46 without substantial friction between the safety shield 30 and the distal opening 46. The proximal flange 90, however, has a greater diameter than the distal opening 46 such that the safety shield 30 cannot be expelled from the housing 22 through the distal opening 46. The safety shield 30 defines a lumen 94 that slidably receives the needle 28. Relative dimensions of the safety shield lumen 94 and the needle 28 are preferably such that the needle 28 is freely slidable within the safety shield lumen 94 without substantial friction between the needle 28 and the lumen 94.

Figure 1A:
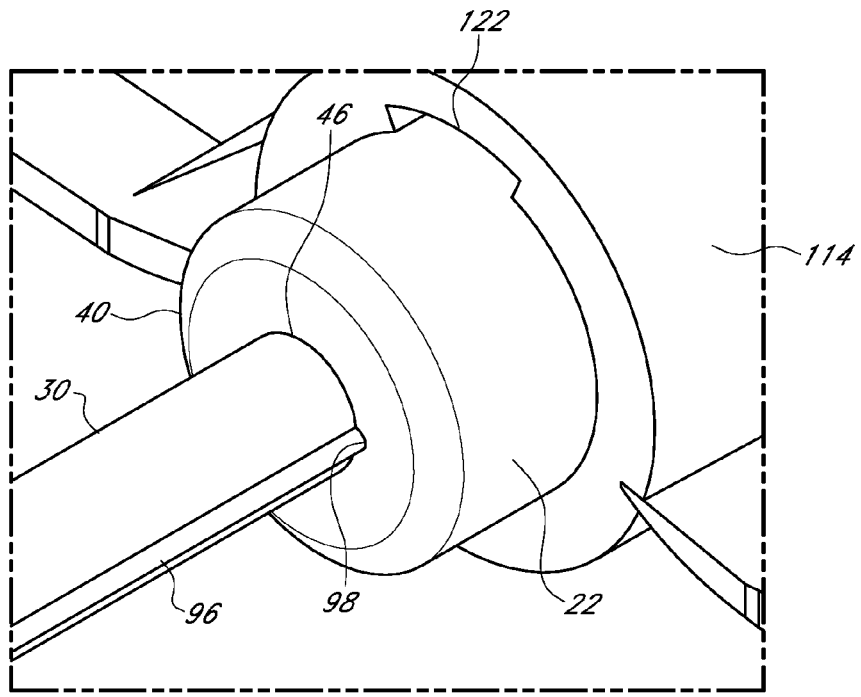
FIG. 1A is a detail view of the portion of FIG. 1 indicated by the box labeled 1A-1A.

With reference to FIG. 1A, which illustrates a detail view of the distal end 40 of the housing 22 where the safety shield 30 emerges through the distal opening 46, the safety shield 30 includes at least one rail 96 that extends longitudinally along the outer surface of the safety shield 30. More than one rail 96 may be provided, such as a second rail 96 disposed diametrically opposite the rail 96 that is visible in FIG. 1A. The distal opening 46 in the housing 22 includes a keyway or slot 98 that receives the rail 96. The keyway 98 is preferably of substantially the same shape as the rail 96, and of slightly greater dimension, such that the keyway 98 and the rail 96 do not interfere with the translatory motion of the safety shield 30 through the distal opening 46, but engagement of the rail 96 in the keyway 98 prevents relative rotation of the safety shield 30 and the housing 22.

Figure 7:
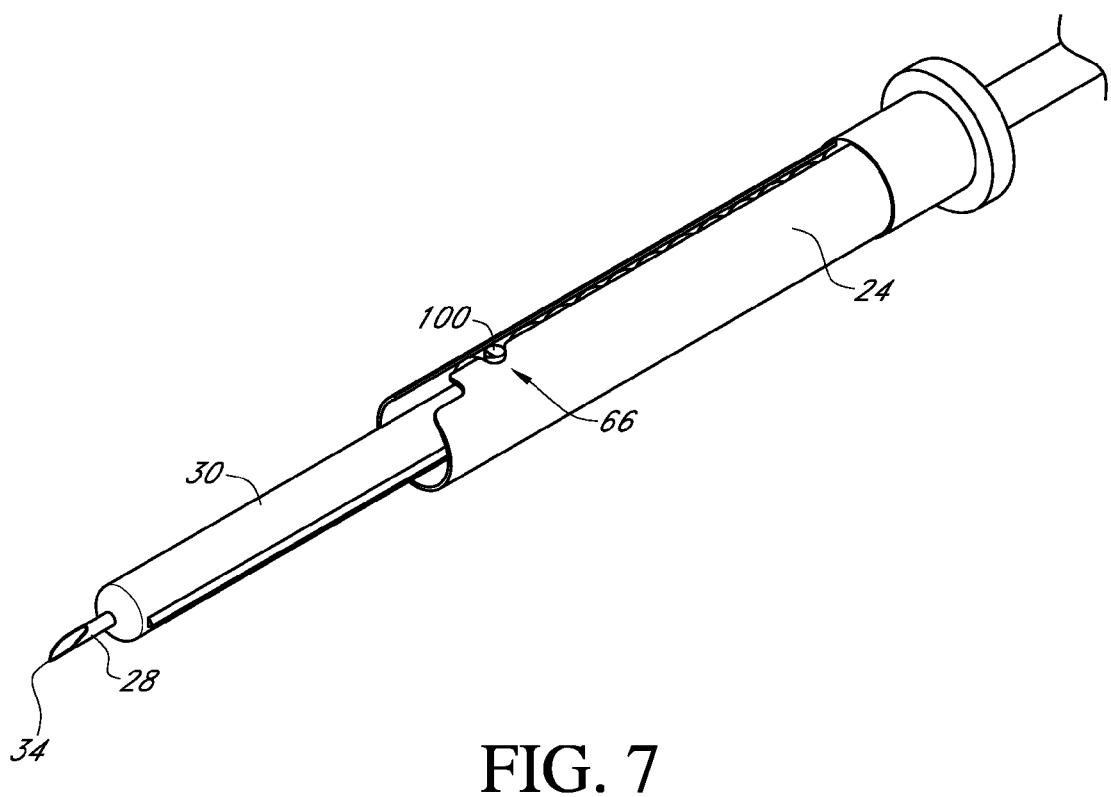
FIG. 7 is a side perspective view of various components of the safety needle assembly of FIG. 1.

With reference to FIG. 6, the safety shield 30 further includes a detent 100 that extends radially outward from the proximal flange 90. In the illustrated embodiment, the detent 100 is circular in cross-section. However, the illustrated configuration is just one example and is not limiting. With reference to FIG. 7, which illustrates the safety shield 30 and the barrel 24 without the housing 22 for clarity, the detent 100 engages the notch 66 on the barrel 24 when the safety needle assembly 20 occupies the pre-activation configuration of FIG. 1. With reference to FIG. 5, a distal face 102 of the notch 66 provides a bearing surface for the detent 100 that resists distal movement of the safety shield 30 along the needle 28, thus keeping the sharp distal tip 34 (FIG. 7) of the needle 28 exposed for use. A proximal face 104 (FIG. 5) of the notch 66 includes a sloped surface that the detent 100 bears against to cause relative rotation of the barrel 24 and the safety shield 30 when the safety shield 30 moves proximally along the needle 28, as described further below.

With reference to FIG. 4, the biasing member 32 is received within the barrel 24. In the illustrated embodiment, the biasing member 32 comprises a spring, more specifically a coil spring. However, the illustrated embodiment is just one example and is not limiting. In the pre-activation configuration of FIGS. 1 and 4, the biasing member 32 is compressed with a proximal end 106 of the biasing member 32 bearing against the distally facing annular shoulder 78 of the needle hub 26 and a distal end 108 of the biasing member 32 bearing against a proximal face 110 of the safety shield 30. When the safety shield 30 translates proximally along the needle 28, as described below, the biasing member 32 compresses further, increasing the magnitude of a spring return force bearing against the safety shield 30, and biasing the safety shield 30 toward the post-activation configuration of FIG. 2, as further described below.

With reference to FIG. 1, the safety needle assembly 20 further includes a wing assembly 112. The wing assembly 112 includes a generally cylindrical body 114 defining an interior passage 116 through which the housing 22 extends, such that the wing assembly 112 is located near the distal end 40 of the housing 22. In the illustrated embodiment, the body is generally cylindrical. However, the illustrated configuration is just one example and is not limiting. For example, the housing can be angular, oblong, oval, or a hollow polyhedron for receiving the housing. Relative dimensions of the body's interior passage 116 and the housing 22 are preferably such that the body 114 is snugly received about the housing 22 so as to restrict relative movement of the wing assembly 112 and the housing 22. The wing assembly 112 may be secured to the housing 22 by any suitable means, such as a friction fit, adhesive, welding, etc.

With further reference to FIG. 1, the wing assembly 112 includes first and second wings 118 that extend laterally in opposite directions from the body 114. The wings 118 are substantially planar and are constructed of a flexible material so that they can conform to contoured surfaces of a patient's body in the area of a blood draw or infusion. Tape (not shown) placed over the wings 118 secures the safety needle assembly 20 to the patient's body. An underside of each wing 118 may include texturing (not shown) to increase the ability of the wings 118 to grip the skin. An optional opening 120 on each wing 118 may be included to facilitate securing the wings 118 to one another.

With reference to FIG. 1A, the wing assembly body 114 includes a channel 122 along its inner surface. The channel 122 overlies the catch 50 on the housing 22 and creates a space into which the catch 50 may deflect when the safety shield 30 moves distally along the needle 28 past the catch 50, as described above.

Figure 8:
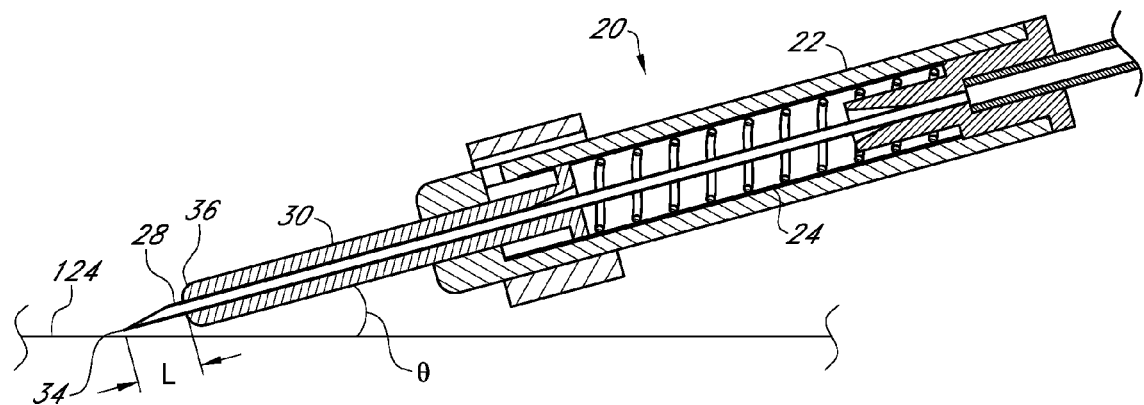
FIG. 8 is a cross-sectional side elevation view of the safety needle assembly of FIG. 1 taken through the cut line labeled 4-4 in FIG. 1.

As described above, embodiments of the present safety needle assembly 20 are configured for use in drawing blood and/or infusing blood or other liquids. The process of inserting the needle 28 into the patient's vasculature is commonly referred to as cannulation. During cannulation, an operator begins with the safety needle assembly 20 in the pre-activation configuration of FIG. 1. The pre-activation configuration is also illustrated in FIG. 8. With reference to FIG. 8, the operator positions the assembly 20 such that the sharp distal tip 34 of the needle 28 is near the patient's skin 124. In the pre-activation configuration as shown, a desired length of the needle 28 adjacent the tip 34 is exposed. In various embodiments, the exposed length L may be any length, such as between about 1 mm and about 10 mm. In one example, the exposed length L may be about 4 mm. The operator positions the assembly 20 such that it forms a desired angle Θ with respect to the patient's skin 124. Θ may be any value, such as between about 5° and about 30°. In one example, Θ may be about 18°.

Figure 9:
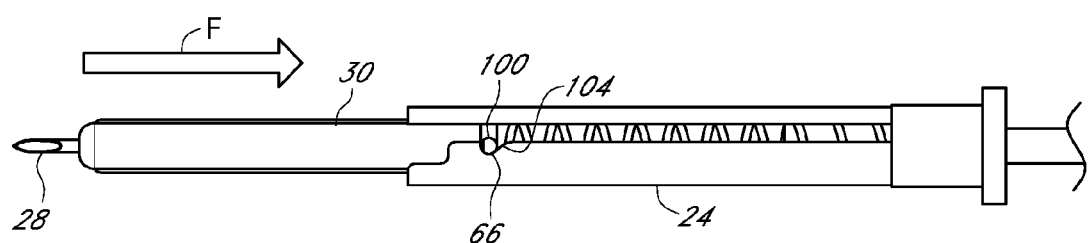
FIG. 9 is a side elevation view of various components of the safety needle assembly of FIG. 1.

With the assembly 20 positioned as in FIG. 8, the sharp distal tip 34 of the needle 28 is closely adjacent to, or abutting, the patient's skin 124, and the distal end 36 of the safety shield 30 is similarly closely adjacent to, or abutting, the patient's skin 124. In this configuration, the safety shield 30 and the barrel 24 define a first relative rotational orientation, which is described above and illustrated in FIGS. 4 and 7. In this first relative rotational orientation, the detent 100 on the safety shield 30 is seated within the notch 66 on the barrel 24, as shown in FIG. 9.

Figure 10:
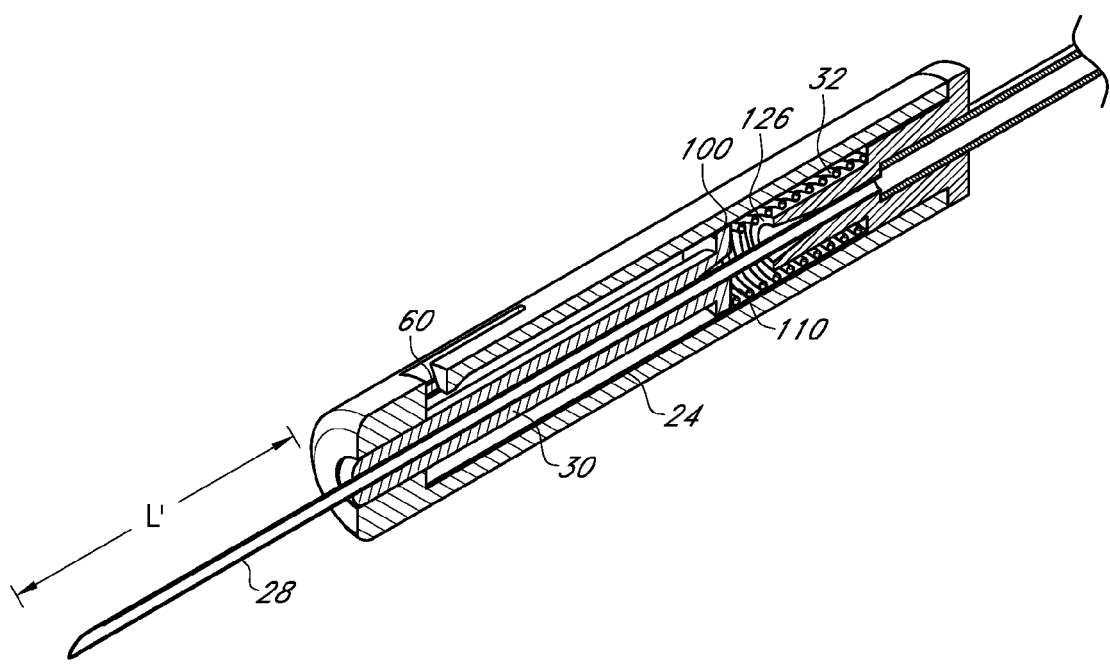
FIG. 10 is a cross-sectional side perspective view of various components of the safety needle assembly of FIG. 1 taken through the cut line labeled 4-4 in FIG. 1.
Figure 11:
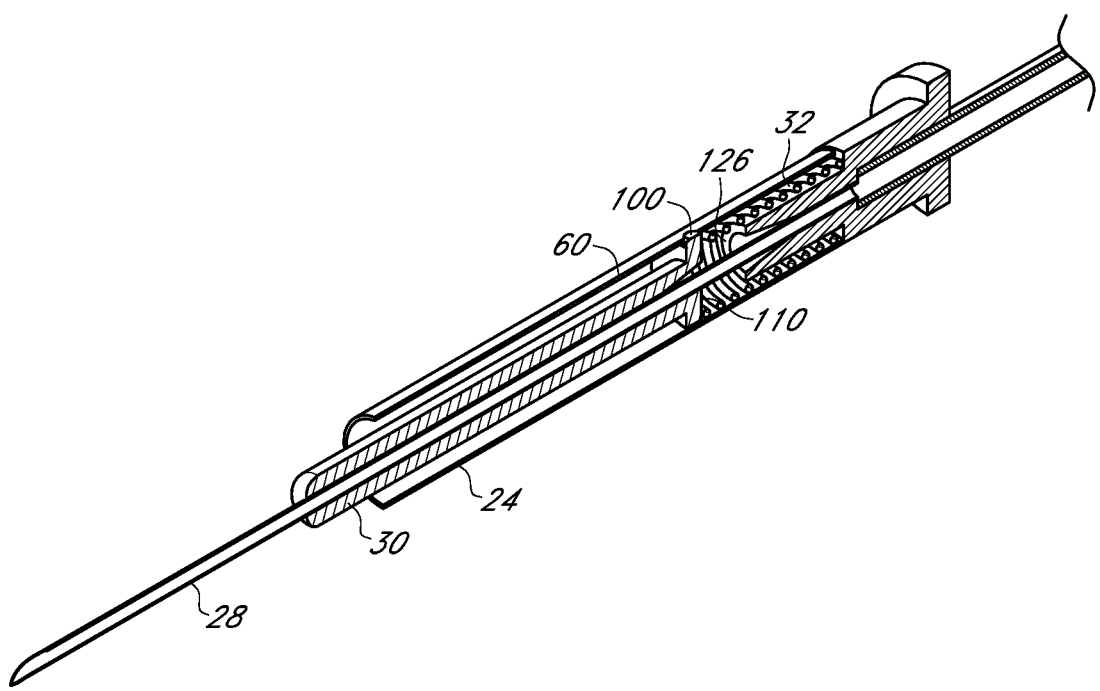
FIG. 11 is a cross-sectional side perspective view of various components of the safety needle assembly of FIG. 1 taken through the cut line labeled 4-4 in FIG. 1.

The operator applies a distally directed force to the assembly 20, such as to the housing 22 and/or the wing assembly 112, to pierce the patient's skin 124 with the needle 28. During this step, the operator preferably does not touch the safety shield 30 so as not to restrict its ability to translate along the needle 28. The motion of the assembly 20 toward the patient's skin 124 forces the distal end 36 of the safety shield 30 against the patient's skin 124, which applies a steadily increasing, proximally directed force F (FIG. 9) on the safety shield 30, forcing the safety shield 30 to translate proximally along the needle 28. The translatory motion of the safety shield 30 along the needle 28 generates rotational motion of the barrel 24 as the detent 100 on the safety shield 30 bears against the sloped proximal surface 104 of the notch 66 on the barrel 24, as described above with reference to FIG. 7, and as shown in FIG. 9. Thus, the safety needle assembly 20 moves toward a second configuration in which the safety shield 30 and the barrel 24 define a second relative rotational orientation. In this second relative rotational orientation, which is illustrated in FIGS. 10 and 11, the detent 100 on the safety shield 30 is positioned within the channel 60 on the barrel 24. The safety shield 30 is thus free to translate along the needle 28, with the detent 100 sliding along the channel 60, until the safety shield 30 reaches a proximal limit. The proximal limit may be defined as a configuration in which the biasing member 32 is compressed as far as possible. In this configuration, again illustrated in FIGS. 10 and 11, the biasing member 32 stores a distally directed spring return force that bears against the proximal face 110 of the safety shield 30. In alternative embodiments, the proximal limit of the safety shield 30 may be defined as a configuration in which the safety shield 30 encounters a barrier, such as the distal face 126 of the needle hub 26, or another barrier (not shown).

FIGS. 10 and 11 illustrate the safety shield 30 at its proximal limit. At this position, a desired length of the needle 28 is exposed. In various embodiments, and with reference to FIG. 10, the exposed length L' may be any length, such as between about 10 mm and about 30 mm. In one example, the exposed length L' may be about 19.5 mm.

When the infusion or blood draw procedure is complete, the operator withdraws the needle 28 from the patient's vasculature. As the needle 28 withdraws, the safety shield 30 moves distally along the needle 28 under the influence of the biasing member 32, which releases the spring return force stored therein as the safety shield 30 moves distally along the needle 28. Because the safety shield 30 and the barrel 24 occupy the second relative rotational orientation during this phase of the process, the detent 100 on the safety shield 30 does not contact the notch 66 on the barrel 24 when the detent 100 reaches the location of the notch 66. Instead, the detent 100, which is positioned in the barrel channel 60, bypasses the notch 66 as the safety shield 30 continues farther distally along the needle 28 toward the post-activation configuration of FIGS. 2 and 12 in which the sharp distal tip 34 of the needle 28 is covered to reduce the likelihood of needlestick.

Figure 12:
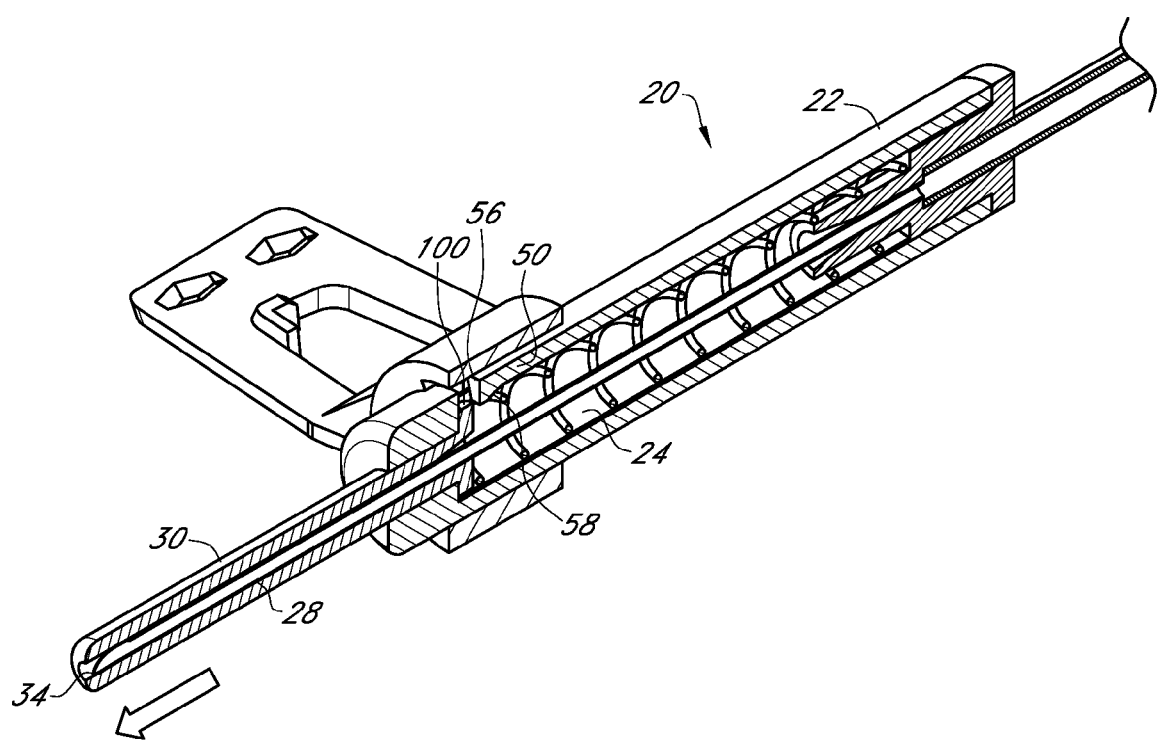
FIG. 12 is a cross-sectional side perspective view of the safety needle assembly of FIG. 2 taken through the cut line labeled 12-12 in FIG. 2.

With reference to FIG. 12, as the safety shield 30 continues moving distally along the needle 28 toward the post-activation configuration, the detent 100 eventually reaches the catch 50 on the housing 22. As the detent 100 passes beneath the catch 50, the detent 100 contacts the ramped inner surface 58 at the distal end 56 of the catch 50, causing the catch 50 to deflect radially outward. As described above, the channel 122 (FIG. 1A) in the inner surface of the wing assembly body 114 provides space into which the catch 50 deflects. When the detent 100 passes distally of the catch 50, the spring return force stored in the catch 50 (which is a leaf spring) moves the catch 50 back to its at rest position, as shown in FIG. 12. Because the catch 50 protrudes into the return path of the detent 100, the catch 50 provides a barrier that prevents the safety shield 30 from moving proximally along the needle 28 by a distance that would be sufficient to re-expose the sharp tip 34 of the needle 28. The sharp distal tip 34 of the needle 28 is thus safely covered by the safety shield 30, thereby reducing the likelihood of needlestick.

As discussed above, some of the present methods may be performed independently of a human and/or animal body, such as for purposes of testing or demonstration. In such embodiments, an operator begins with the safety needle assembly 20 in the pre-activation configuration of FIG. 1. The operator then may translate the safety shield 30 proximally along the needle 28 by grasping the housing 22 with the fingers on one hand, grasping the safety shield 30 with the fingers on the opposite hand, and pushing the safety shield 30 proximally with respect to the needle 28 and the housing 22. The proximal translation of the safety shield 30 along the needle 28 rotates the barrel 24 and disengages the detent 100 on the safety shield 30 from the notch 66 on the barrel 24. When the operator releases the safety shield 30, the spring return force in the biasing member 32 translates the safety shield 30 distally along the needle 28 until the safety shield 30 reaches the post-activation configuration of FIG. 2.

The various component parts of the present safety needle assembly 20 may be constructed of suitable medical grade materials having material properties that provide each component with desired characteristics, which characteristics may vary from one component to another. For example, certain components such as the housing 22, the barrel 24, the needle hub 26, the safety shield 30 and/or the wing assembly 112 may be constructed of medical grade plastic materials, including, without limitation, nylon, polyethylene, polypropylene, polyurethane, ethylene-vinyl acetate (EVA), polyether block amide (PEBAX), acrylonitrile butadiene styrene (ABS), polyether ether ketone (PEEK), polytetrafluoroethylene (PTFE), thermoplastic polyetherimide (ULTEM), etc. Certain other components, such as the needle 28 and/or the biasing member 32, may be constructed of medical grade metal materials, including, without limitation, stainless steel, titanium, cobalt-chromium, etc. The foregoing examples should not be construed as limiting. For example, components indicated as being plastic may in some cases be constructed of other materials, such as metals, and components indicated as being metal may in some cases be constructed of other materials, such as plastics.

Method of manufacturing or making and method of using the safety needle assemblies and their components are within the scope of the present disclosure.

The above description presents various embodiments of the present invention, and the manner and process of making and using them, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention.

What is claimed is:

1. A safety needle assembly, comprising:
   a housing including a proximal end and a distal end, the housing defining an interior space;
   a barrel rotatably received within the interior space of the housing;
   a needle hub received within the proximal end of the housing;
   a needle extending distally from the needle hub, through the barrel, and through the distal end of the housing, the needle including a sharp distal tip at an end of a needle shaft;
   a safety shield defining a lumen and received within the interior space of the housing, the safety shield extending distally from the housing through the distal end of the housing, the needle extending through the lumen of the safety shield with the sharp distal tip and at least part of the needle shaft located distally of a distal-most end of the safety shield and exposed from the safety shield in a pre-activation configuration; and
   a biasing member received within the barrel and extending between the needle hub and the safety shield;
   wherein the safety needle assembly includes a first configuration in which the safety shield and the barrel define a first relative rotational orientation; and
   wherein the safety needle assembly includes a second configuration in which the safety shield and the barrel define a second relative rotational orientation; and
   wherein the safety shield includes a detent that engages a notch on the barrel when the safety needle assembly occupies the first configuration, and that the notch includes a sloped surface proximal of the detent.

2. The safety needle assembly of claim 1, wherein when the safety needle assembly occupies the first configuration the safety shield engages the barrel to prevent distal translation of the safety shield relative to the needle.

3. The safety needle assembly of claim 1, wherein the detent bears against the sloped surface when the safety shield moves proximally relative to the barrel, causing the barrel to rotate relative to the safety shield toward the second relative rotational orientation.

4. The safety needle assembly of claim 3, wherein the detent extends radially outward from the safety shield.

5. The safety needle assembly of claim 2, wherein the barrel includes a longitudinal channel and the detent is slidable within the channel when the safety shield and the barrel occupy the second relative rotational orientation.

6. The safety needle assembly of claim 5, wherein the channel extends through a sidewall of the barrel from a proximal end to a distal end of the barrel.

7. The safety needle assembly of claim 1, wherein when the safety needle assembly occupies the second configuration the barrel does not constrain distal translation of the safety shield relative to the needle.

8. The safety needle assembly of claim 1, wherein the biasing member biases the safety shield in the distal direction when the safety needle assembly occupies the first configuration and when the safety needle assembly occupies the second configuration.

9. The safety needle assembly of claim 8, wherein the safety shield moves distally relative to the needle to cover the sharp distal tip of the needle when a distally directed force exerted by the biasing member on the safety shield overcomes a proximally directed force exerted on the safety shield.

10. The safety needle assembly of claim 9, wherein when the safety shield covers the sharp distal tip of the needle the housing prevents the safety shield from moving proximally with respect to the needle by a distance sufficient to expose the sharp distal tip of the needle.

11. The safety needle assembly of claim 10, wherein the housing includes a catch configured to deflect to allow the safety shield to pass when the safety shield moves in the proximal-to-distal direction relative to the housing and configured to block movement of the safety shield in the distal-to-proximal direction relative to the housing.

12. The safety needle assembly of claim 11, wherein the catch comprises a leaf spring.

13. The safety needle assembly of claim 1, wherein the safety shield engages the housing to prevent the safety shield from rotating relative to the housing.

14. The safety needle assembly of claim 13, wherein the safety shield includes at least one rail that extends longitudinally along an outer surface of the safety shield and that is slidably received within at least one indentation in the housing.

15. The safety needle assembly of claim 1, further comprising a wing assembly including wings extending laterally from the safety needle assembly and configured to facilitate securing the safety needle assembly to a patient.

16. The safety needle assembly of claim 1, wherein the biasing member is a spring.

17. A method of manufacturing a safety needle assembly comprising:
   forming a housing supporting a barrel and a needle hub, the barrel being rotatably received within the housing;
   extending a needle distally from the needle hub, said needle including a sharp distal tip at an end of a needle shaft;
   positioning a safety shield over the needle so that the sharp distal tip extends distally of and is exposed from a distal end of the safety shield in a first configuration and in a pre-activation configuration;
   wherein the safety shield is slidably disposed inside the barrel and engages the barrel to prevent translation of the safety shield distally along the needle;
   wherein the safety shield is translatable distally along the needle to cover the sharp distal tip of the needle in a post-activation configuration;
   wherein the barrel is rotatable with respect to the safety shield when the safety shield translates proximally along the needle to disengage the safety shield from the barrel to permit translation of the safety shield distally along the needle and that the safety shield includes a detent that engages a catch on the barrel when the safety needle assembly occupies the first configuration, and that the catch includes a sloped surface proximal of the detent.

18. The method of claim 17, further comprising a biasing member to apply a distally directed force to the safety shield.

19. The method of claim 18, wherein the biasing member is received within the barrel and extends between the needle hub and the safety shield.

20. The method of claim 17, wherein the biasing member is a spring.

21. The method of claim 17, wherein the detent bears against the sloped surface when the safety shield translates proximally along the needle, causing the barrel to rotate with respect to the safety shield.

* * * * *